United States Patent [19]

Bahr

[11] 4,388,105

[45] Jun. 14, 1983

[54] HERBICIDAL CYCLIC SULFONAMIDES OF PHENOXYBENZOIC ACIDS

[75] Inventor: James T. Bahr, Hopewell, N.J.

[73] Assignee: Rhone-Poulenc Agrochimie, Lyons, France

[21] Appl. No.: 287,350

[22] Filed: Jul. 27, 1981

[51] Int. Cl.³ .................. A01N 43/72; C07D 279/02
[52] U.S. Cl. ........................................ 71/91; 544/49
[58] Field of Search .............................. 544/49; 71/91

[56] References Cited

U.S. PATENT DOCUMENTS 3,408,346 10/1968 Satzinger ............................ 544/49
3,784,635 1/1974 Theissen ............................ 71/98 X
4,063,929 12/1977 Bayer et al. ......................... 71/115
4,209,318 6/1980 Johnson ............................. 71/105
4,285,723 8/1981 Cartwright et al. ................. 71/103

FOREIGN PATENT DOCUMENTS 49-62637 6/1974 Japan .
54-151943 11/1979 Japan .

Primary Examiner—Richard Raymond
Attorney, Agent, or Firm—Morgan, Finnegan, Pine, Foley & Lee

[57] ABSTRACT

There are provided herbicidal cyclic sulfonamides of phenoxybenzoic acids.

5 Claims, No Drawings

HERBICIDAL CYCLIC SULFONAMIDES OF PHENOXYBENZOIC ACIDS

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Pat. which describe such compounds and the like include U.S. Pat. Nos. 3,652,645; 3,784,635; 3,873,302; 3,983,168; 3,907,866; 3,798,276; 3,928,416; and 4,063,929.

SUMMARY OF THE INVENTION

This invention provides certain herbicidal compounds of the formula:

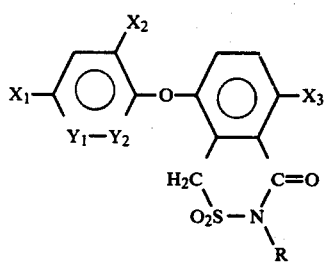

where:
(i) $Y_1$ is N or CH;
(ii) $Y_2$ is N or $CX_4$; provided that $Y_1$ is not N when $Y_2$ is $CX_4$; and
(iii) $X_1$, $X_2$, $X_3$, $X_4$ and R are groups which are capable of being incorporated into formula I and which collectively impart herbicidal activity thereto.

With respect to compounds of formula I which are capable of forming salts (e.g., where R is H), the invention also provides agronomically acceptable salts (e.g., alkali metal salts such as sodium salts or ammonium salts, e.g, of the formula $(C_1-C_6 \text{ alkyl})_n NH_{4-n}$ (where n is 0–4) of compounds of formula I.

Examples of the groups $X_1$, $X_2$, $X_3$, $X_4$ and R are as follows:

$X_1$ and $X_2$ may be the same or different and may be selected from the group consisting of halo (e.g., Cl, Br or F) or $CF_3$;
$X_3$ may be $NO_2$ or halo (e.g., Cl, Br or F);
$X_4$ may be H, halo (e.g., Cl, Br or F) or $CF_3$; and
R may be H or substituted or unsubstituted hydrocarbyl (e.g., having from 1 to 12 carbon atoms such as $C_1-C_{12}$ alkyl).

A preferred form of forumula I is represented by the formula

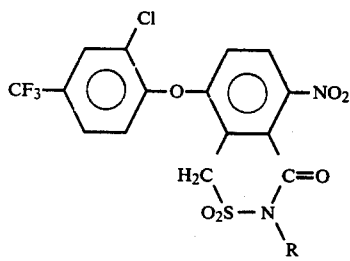

Preferred compounds according to the present invention are:

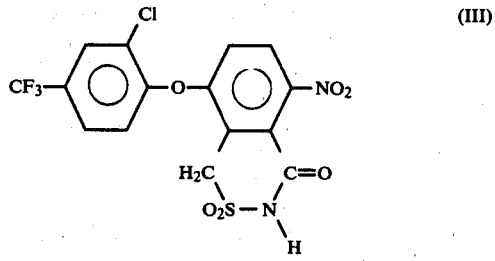

and sodium, potassium and ammonium salts of formula III.

Compounds of formula I may be prepared by
(1) Oxidation of the appropriate benzyl mercaptan to the sulfonic acid:

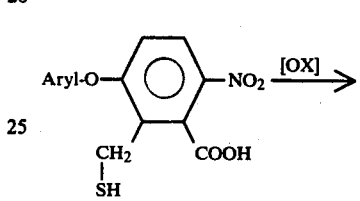

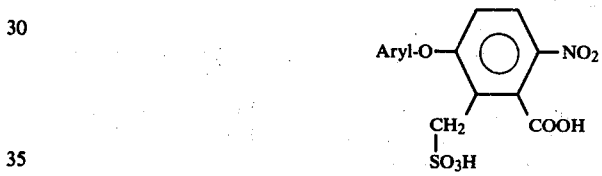

(2) Formation of the cyclic amide:

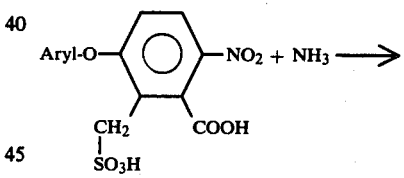

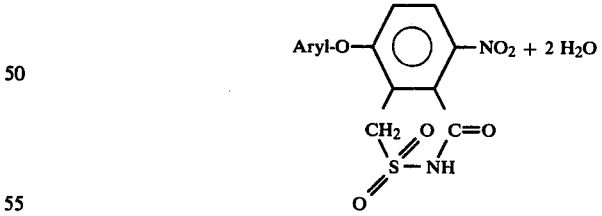

The compounds of this invention can be applied in various ways to achieve herbicidal action. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cottom seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice, herbicidal application is measured in terms of pounds of herbicide applied per acre. The compounds of this invention are effective herbicides when applied in herbicidal amounts, e.g., at rates between about 0.03 pound and about 10 pounds per acre.

What is claimed is:

1. A herbicidal compound of the formula:

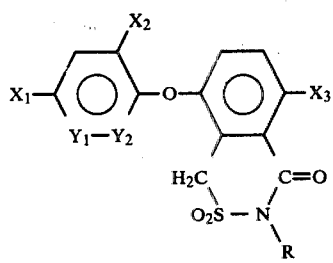

where:
(i) $Y_1$ is N or CH;
(ii) $Y_2$ is N or $CX_4$, provided that $Y_1$ is not N when $Y_2$ is $CX_4$;
(iii) $X_1$ and $X_2$ are the same or different and selected from the group consisting of halogen or $CF_3$;
(iv) $X_3$ is $NO_2$ or halogen;
(v) $X_4$ is H, halogen or $CF_3$; and
(vi) R is H or $C_1$ to $C_{12}$ alkyl.

2. A herbicidal compound of the formula:

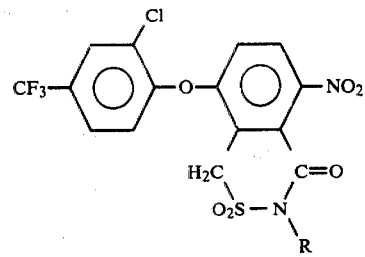

wherein:
R is H or a $C_1$ to $C_{12}$ alkyl.

3. A herbicidal compound selected from the group consisting of:

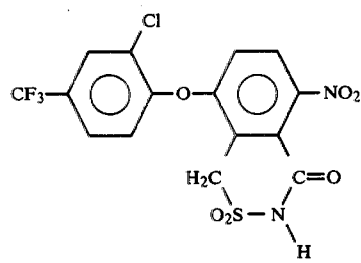

and sodium, potassium and ammonium salts of formula III.

4. A herbicidal composition comprising an effective amount of a compound according to any one of claims 1 to 3, and an agronomically acceptable carrier.

5. A method for combating unwanted plants which comprises contacting them with a herbicidally effective amount of a compound according to any one of claims 1 to 3.

* * * * *

UNITED STATES PATENT AND TRADEMARK OFFICE
CERTIFICATE OF CORRECTION

PATENT NO. : 4,388,105
DATED : Jun. 14, 1983
INVENTOR(S) : James T. Bahr

It is certified that error appears in the above-identified patent and that said Letters Patent is hereby corrected as shown below:

At column 4, lines 29-30 delete "of formula III" and insert therefor -- thereof.-- .

Signed and Sealed this

Sixth Day of September 1983

[SEAL]

Attest:

GERALD J. MOSSINGHOFF

Attesting Officer

Commissioner of Patents and Trademarks